United States Patent [19]

Bouillie et al.

[11] 4,176,954
[45] Dec. 4, 1979

[54] EQUIPMENT FOR MEASURING THE LENGTH OF DIELECTRIC ELEMENTS TRANSMITTING OPTICAL FREQUENCIES

[76] Inventors: Rémy A. Bouillie, route de Tréguier; Gérard M. Beauvillain, Résidence Corlay, both of Lannion, France, 22300

[21] Appl. No.: 874,688

[22] Filed: Feb. 2, 1978

Related U.S. Application Data

[63] Continuation of Ser. No. 592,166, Jul. 1, 1975, abandoned.

[30] Foreign Application Priority Data

Jul. 26, 1974 [FR] France ............................. 74 25995

[51] Int. Cl.$^2$ ..................... G01N 21/00; G01B 11/02
[52] U.S. Cl. .................................. 356/73.1; 356/383
[58] Field of Search ............... 250/560; 356/128, 156, 356/161, 73.1, 382, 383

[56] References Cited

U.S. PATENT DOCUMENTS 3,545,862 12/1970 Ackerman ................................. 356/5
3,728,026 4/1973 Idestrom et al. ......................... 356/5

OTHER PUBLICATIONS

"Optical Ranging System Using Laser Transmitter", Stitch et al.; Electronics; Apr. 21, 1961; pp. 51–53.

*Primary Examiner*—Vincent P. McGraw
*Attorney, Agent, or Firm*—Abraham A. Saffitz

[57] ABSTRACT

An equipment for measuring length or refractive index of a dielectric element capable of transmitting optical frequency signals, for instance an optical wave guide. The used method consists in making at least one measurement of the propagation time of a light impulse over a length of the said element, and deducing therefrom the unknown length or index, if one of the latter is previously known. The equipment includes an injector of light signals, a separator dividing each light pulse signal into a delayed and a non-delayed one respectively transmitted through a first and a second path one of which contains the dielectric element to be measured and the other of which is used as a comparison one, a detector at the output of each of said paths, and a viewing element displaying the outputs of both detectors on a common screen, for instance that of an oscilloscope whereby the propagation time difference between said paths is translated into the spacing between the said outputs observed on said screen.

1 Claim, 4 Drawing Figures

EQUIPMENT FOR MEASURING THE LENGTH OF DIELECTRIC ELEMENTS TRANSMITTING OPTICAL FREQUENCIES

This is a continuation, of application Ser. No. 592,166, filed July 1, 1975, now abandoned.

BACKGROUND OF THE INVENTION

1. Field of the Invention:

The present invention relates to an equipment for measuring the length or the refractive index of a dielectric element for the transmission of signals of optical frequencies.

2. Description of the Prior Art:

It is known that the availability having dielectric elements of very low attenuation in the optical wavelengths has made it possible to use of such elements in systems for the transmission of light over more or less long distances. In these systems, the use of these dielectric elements requires for them a protection or covering in the form of cables. For various reasons (cabling, utilization, etc.), one may have to know precisely certain parameters of a dielectric element, in particular its length and its refractive index.

The dielectric element to be measured is constituted by an optical fibre, that is to say an element composed of one or more dielectrics such as glass, silica, plastic material, etc., but in all cases capable of conducting light.

This optical fibre may form part of a conductor constituted by one or more fibres transmitting the same signal in parallel, or else of a cabling element constituted by one or more conductors or even of a complete cable constituted by one or more such cabling elements.

It is known in the art to use a telemetric device for measuring distance in the air, such device comprising a light impulse laser, the impulses of which are reflected by a target, and transmitted therefrom over a first path to a photomultiplier and an oscilloscope, these same impulses being also transmitted along a second path to a photoelectric cell and to said oscilloscope. In this arrangement, the transmission of the light impulses is effected in air, whereas in the invention, as explained hereinafter, the transmission of said impulses is effected in a refracting medium having a refractive index of value n. It is therefore obvious that such a known device does not permit the measurement of a refractive index.

It is likewise known to measure the load or the force applied to a test piece of a compressible medium by measuring the variation in length of said test piece due to said force, the measuring being effected with the aid of electric impulses applied by a crystal forming the base of the said test piece, said electric impulses being transformed into acoustic impulses in the said medium. The transmission of the acoustic waves in a medium always obeys a different law from those of light waves utilized in the invention.

To solve this problem, the present invention proposes a method characterized in that it consists essentially in making at least one measurement of the duration of passage ($t_1 - t_0$) of a light impulse over the length L of the element to be measured, having a refractive index n, and in applying the formula:

$$t_1 - t_0 = nL/c$$

where c is the velocity of light in vacuo, to obtain either one of the values of n or of L, knowing the other.

OBJECT OF THE INVENTION

An object of the present invention is to provide measuring equipment for dielectric elements using the above method.

SUMMARY OF THE INVENTION

The measurement equipment comprises a diode laser source of periodically repeated short duration light pulses, an electrical pulse generator, a current amplifier connecting the generator to the diode laser source, and the diode laser source. Optical separator means located along the emitting axis of the laser light pulses divide the light signal into a first signal of light pulses taking a first path and a second signal of light pulses taking a second path to the input end of the dielectric element.

First and second detecting means receive the first and second light signals respectively and convert these into first and second electrical signals respectively. The second detecting means receives the second light signals at the output end of the dielectric element which has been delayed by travelling through the dielectric element.

An electrical time measurement means receives the first and second electrical signals for measuring the time delay between a light pulse of the first light signal and a light pulse of the second delayed light signal.

According to a preferred embodiment of the invention, the electrical pulse generator comprises means for controlling the recurrence frequency of the light pulses. Also, the propagation time of the second light signal through the dielectric element is measured from the observed recurrence frequency when the successive pulses of the first electrical signal coincide with the delayed pulses of the second electrical signal.

BRIEF DESCRIPTION OF THE DRAWING

The invention will be better understood on reading the following description of some of its embodiments and on examining the corresponding annexed drawings in which.

DESCRIPTION OF THE PREFERRED EMBODIMENT

Let the length of a dielectric element to be measured be L, and its refractive index be n. If this element receives at a first end or input a light impulse at the instant $t_0$, the latter arrives at the other end or output at the instant $t_1$, and one may write:

$$t_1 - t_0 = nL/c$$

where c is the velocity of light in vacuo.

From the knowledge, either by measurement or by previous knowledge of n and c, the measurement of ($t_1 - t_0$) allows to obtain L by the following relationship:

$$L = c(t_1 - t_0)/n$$

From the knowledge, either by measurement or by previous knowledge of L and c, the measurement of $(t_1-t_0)$ allows to obtain n by the relationship:

$$n = c(t_1-t_0)/L$$

To measure the interval of time $(t_1-t_0)$ use is made of an equipment for dividing a light signal S of light pulses with a determined recurrence frequency f into a first and a second light signals $S_1$, $S_2$, the signal $S_2$ being transmitted into a first end of the dielectric element E to be measured, and for displaying the signal $S_1$ and the signal $S_2$ transmitted by the other end of the dielectric element E.

Figure 1:
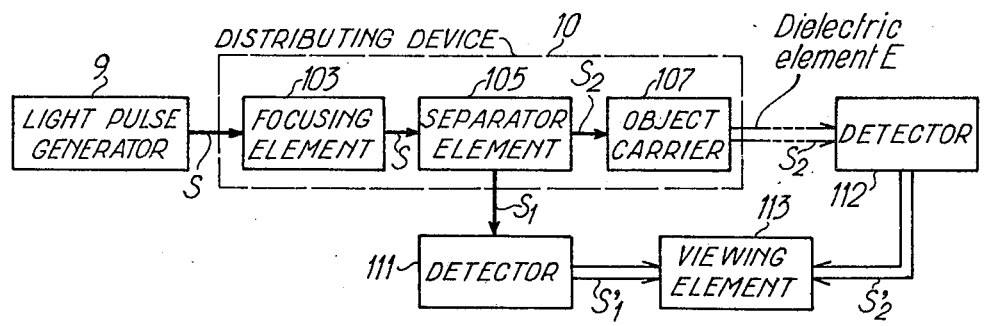
FIG. 1 is a block diagram illustrating the principle of a measuring equipment according to the invention.

In a general manner this equipment is shown in FIG. 1 and comprises a generator 9 generating the light signal S, a distributing device 10 receiving the signal S and distributing the signals $S_1$, $S_2$ and a viewing element 113.

The generator 9 periodically emits sufficiently short light impulses; that is to say, impulses of duration clearly less than the value $(t_1-t_0)$ to be measured, to constitute the light signal S. The recurrence frequency of these impulses is selectively fixed or variable. The source included in the generator 9 is, as desired either a gas or solid laser comprising a cell which effects a selection of modes, for instance an electroluminescent diode or an electroluminescent diode with laser effect (laser diode). It is desirable to choose the wavelength emitted from the source in a band of wavelengths in which the dielectric element to be measured has a minimum attenuation. The device 10 allows the light signal S to be divided into the two light signals $S_1$ and $S_2$. A first optical path between the device 10 and the detector element 111 is travelled by the light signal $S_1$ and a second optical path between the device 10 and the output of the dielectric element E is travelled by the light signal $S_2$.

In this end, the distributing device 10 comprises a focusing element 103, a separator element 105 and an object carrier 107.

The focusing element 103 permits focussing the light at the input of the dielectric element to be measured E. This may be at will a simple lens, a system of lenses such as a microscope objective, a lens with an index gradient or any other suitable system for the focusing of light.

The separator element 105 permits dividing of the light signal S issued from the preceding focusing element 103 into the two signals $S_1$, $S_2$. The separator element 105 is advantageously covered with antireflective layers on certain of its faces, to obviate parasitic reflections.

The object carrier 107 allows to fasten the element to be measured E at the focus of the focusing element 103 seen through 105. This object is carrier designed for being adapted easily to all the possible types of elements to be measured.

In a preferred embodiment the focusing element 103 permits focusing the light at the input of the dielectric element E or the object carrier 107 through the separator element 105 which is interposed between the element 103 and the object carrier 107.

Two detector elements 111, 112 transform the light signals received $S_1$, $S_2$ into electrical signals $S_1'$, $S_2'$ respectively. These detectors may each be a breakdown photodiode, a photomultiplier or any other suitable detector element. The two detectors 111, 112 are not necessarily of the same kind, but, if different, they should have equivalent characteristics (such as response time and rise time) so as not to comprise the precision of the measurement. It should be noted, however, that the detector element 111 is not absolutely necessary; in fact, any electric signal synchronous with the optical emission (generator of electric control impulses, for example) may be utilized as the element 111; in such a case, there is no longer any need to use the separator element 105.

The viewing element 113 allows displaying of the signals $S_1'$, $S_2'$ on the same screen, in view of their measurement.

Figure 2:
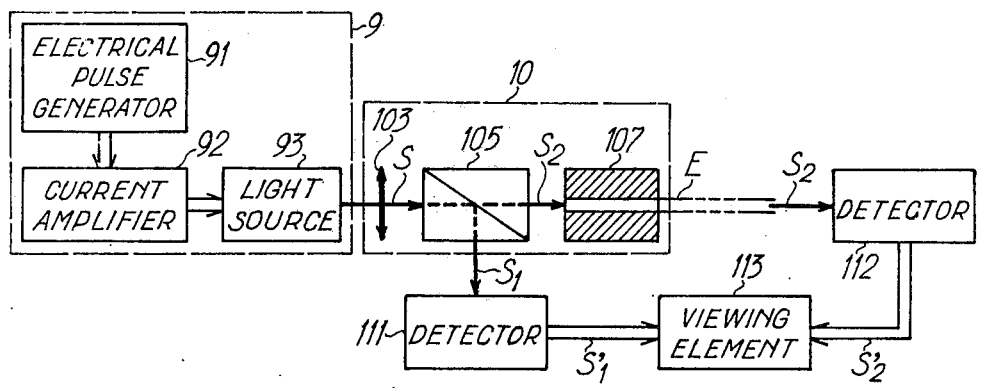
FIG. 2 is a block diagram of a particular measuring equipment according to the invention.

In accordance with the present invention a preferred embodiment of the measuring equipment is represented in FIG. 2 as hereinafter explained.

Assuming the elements to be measured to have their minimum attenuation wavelength between 8000 and 9000 Å, one selects as source of light impulses a laser diode capable of emitting this wavelength. The elements of the light pulses generator 9 of the equipment are as follows:

a source of light impulses is such a laser diode transmitting, on the said wavelength, light impulses of a duration of 5 nanoseconds, the peak power emitted being a few hundred milliwatts;

the element 101 is supplied with power from a generator 9 delivering to the source 93 electrical impulses of variable and adjustable frequency in a wide range comprised from a few hertz to a few hundreds of megahertz; and a current amplifier 92 interconnected to the generator 91 and the light pulse source 93 and supplying an adjustable current of several amperes, for exciting any type of laser diode included in the source 93.

The focussing element 103 is a microscope objective of magnification 10.

The separator element 105 is a Lummer cube treated to be anti-reflective.

The object carrier 107 allows adjusting the position and the direction of the element to be measured.

The detector elements 111, 112 include each an electro-optical transducer converting the undelayed light signal $S_1$ and the delayed light signal $S_2$ into electrical signals $S_1'$, $S_2'$ respectively. The transducers are two breakdown photodiodes of the same type having consequently the same response time and same rise time. They are both loaded by 50 ohms.

The viewing element 113 is an oscilloscope.

Figure 3A:
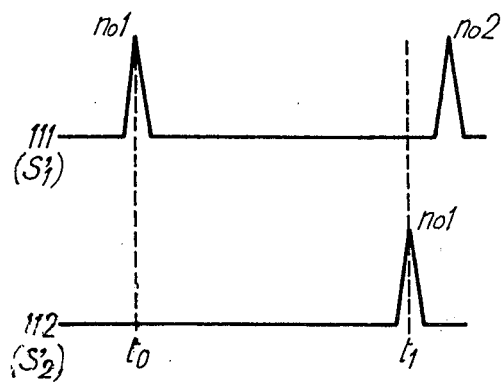
FIGS. 3a and 3b are representative time diagrams corresponding to two possible measuring methods.

Two methods may be used to effect the measurement:

In a first method (FIG. 3a) the time interval $(t_1-t_0)$ is measured by direct reading on the screen of the oscilloscope.

Figure 3B:
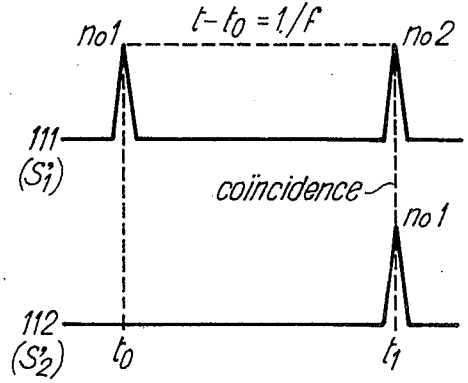

In a second method (FIG. 3b) a source of light impulses with variable and adjustable recurrence frequency of value f (as in the above example) is used and this frequency is so adjusted that when viewed on the screen of the oscilloscope, the delayed impulse No. 1, detected by the detector element 112 coincides in time with the non-delayed impulse No. 2 detected by the detector element 111. One benefits then from a better accuracy: the delay sought $(t_1-t_0)$ is obviously given by the reciprocal of the frequency of measurement.

One can then measure selectively either the refractive index n or the length L of the dielectric element E to be measured.

In the first case (measurement of n) it is necessary to determine with sufficient precision the length L of a sample (for example, having a length of a few meters) of the element to be measured.

In the second case (measurement of L) it is necessary to know with sufficient precision the value of the refractive index n. It is then advantageous to take a sample of known length L' of the same kind as the element to be measured, to make a first measurement of delay $(t_1'-t_0')$ on this sample from which the index n can be determined by:

$$n = c(t_1' - t_0')/L'$$

Then a second measurement is carried out on the dielectric element E whose length L is to be measured, from which the length can be obtained by:

$$L = c(t_1 - t_0)/n$$

that is to say $$L = (t_1 - t_0)/(t_1' - t_0') \, L'$$

In selecting the coincidence method for the measuring of the two delays the error in the length L of a dielectric element of refractive index of the order of 1.5 (common type glass) is about 20 cm. This error is completely independent of the length L to be measured and only depends on the measuring equipment.

What we claim is:

1. Equipment for measurement of propagation time for light waves passing through a dielectric element comprising:

- a diode laser source of short periodically repeated bursts of light impulses serving as the light waves passing through said dielectric element;
- an adjustable electrical pulse generator for generating an adjustable repetition frequency and a current amplifier connecting said generator to said laser source;
- a holder for said dielectric element;
- an optical separator interposed along the axis of the laser beam of light emitted by said laser source between said source and said holder which divides the light impulses of said laser beam into a first path of light pulses and a second path of light pulses directed into said dielectric element on said holder;
- first detecting means in said first path to receive said light pulses not directed into said dielectric element and convert said light pulses into first electric signals;
- optical focusing means interposed along the axis of the laser beam of light between the laser source and said optical separator to direct said light pulses of said second path into the inlet side of said dielectric element;
- second detecting means receiving the light pulses which emerge from the output side of said dielectric element after being delayed by passing through the dielectric medium of said element which converts the light pulses into second electrical signals; and
- display means for said first and second detecting means for displaying successive pulses of said first electrical signals and successive pulses of said second electrical signals in which light impulses of adjustable repetition frequency achieve visual coincidence on the display of a delayed impulse succeeded by a non-delayed impulse.

* * * * *